(12) United States Patent
Bang-Andersen et al.

(10) Patent No.: US 8,450,324 B2
(45) Date of Patent: May 28, 2013

(54) CRYSTALLINE BASE OF TRANS-1-((1R,3S)-6-CHLORO-3-PHENYL-INDAN-1-YL)-3,3-DIMETHYLPIPERAZINE

(75) Inventors: Benny Bang-Andersen, Copenhagen (DK); Heidi Lopez de Diego, Nærum (DK)

(73) Assignee: H. Lunbeck A/S, Valby (DK)

( * ) Notice: Subject to any disclaimer, the term of this patent is extended or adjusted under 35 U.S.C. 154(b) by 754 days.

(21) Appl. No.: 12/628,613

(22) Filed: Dec. 1, 2009

(65) Prior Publication Data

US 2010/0105699 A1    Apr. 29, 2010

Related U.S. Application Data

(63) Continuation of application No. 11/816,394, filed as application No. PCT/DK2006/000088 on Feb. 14, 2006, now Pat. No. 7,648,991.

(60) Provisional application No. 60/653,419, filed on Feb. 16, 2005.

(30) Foreign Application Priority Data

Feb. 16, 2005   (DK) .................................. 2005 00239

(51) Int. Cl.
 *A61K 31/4965*    (2006.01)
(52) U.S. Cl.
 USPC .................................................... 514/255.03
(58) Field of Classification Search
 USPC .................................................... 514/255.03
 See application file for complete search history.

(56) References Cited

U.S. PATENT DOCUMENTS

| | | | |
|---|---|---|---|
| 4,031,216 A | 6/1977 | Cyrus et al. |
| 4,443,448 A | 4/1984 | Bogeso |
| 4,616,086 A | 10/1986 | Witte et al. |
| 5,026,853 A | 6/1991 | Van Daele et al. |
| 5,466,806 A | 11/1995 | Belleau et al. |
| 5,561,057 A | 10/1996 | Trani et al. |
| 5,807,855 A | 9/1998 | Bogeso et al. |
| 5,807,897 A | 9/1998 | Warawa et al. |
| 6,103,719 A | 8/2000 | Esser et al. |
| 6,153,611 A | 11/2000 | Mattson et al. |
| 6,410,794 B1 | 6/2002 | Zinnen et al. |
| 6,444,854 B1 | 9/2002 | Dapremont et al. |
| 6,455,736 B1 | 9/2002 | Zinnen et al. |
| 6,506,940 B1 | 1/2003 | Jadav et al. |
| 6,635,645 B1 | 10/2003 | Lochead et al. |
| 7,648,991 B2 | 1/2010 | Bang-Andersen et al. |
| 7,767,683 B2 | 8/2010 | Lopez de Diego et al. |
| 7,772,240 B2 | 8/2010 | Bang-Andersen et al. |
| 2010/0105699 A1 | 4/2010 | Bang-Andersen et al. |

FOREIGN PATENT DOCUMENTS

| | | |
|---|---|---|
| EP | 0035363 A1 | 9/1981 |
| EP | 0638073 B1 | 6/2000 |
| JP | 06184132 | 5/1994 |
| JP | 2000/351773 A | 12/2000 |
| WO | 93/08799 A1 | 5/1993 |
| WO | 93/22293 A1 | 11/1993 |
| WO | 95/15299 A1 | 6/1995 |
| WO | 99/42107 A1 | 8/1999 |
| WO | 99/61426 A1 | 12/1999 |
| WO | 99/62893 A2 | 12/1999 |
| WO | 00/12073 A1 | 3/2000 |
| WO | 00/34284 A1 | 6/2000 |
| WO | 00/75172 A2 | 12/2000 |
| WO | 00/76961 A1 | 12/2000 |
| WO | 00/78708 A1 | 12/2000 |
| WO | 2005/016900 A1 | 2/2005 |
| WO | 2005/016901 A1 | 2/2005 |
| WO | WO 2005/016901 * | 2/2005 |
| WO | 2006/086985 A1 | 8/2006 |
| WO | 2006/086986 A1 | 8/2006 |

OTHER PUBLICATIONS

Adler, L., et al., "Schizophrenia, sensory gating, and nicotinic receptors", Schizophrenia Bulletin, 1998; 24 (2):189-202.

Allan, G., et al., "One-pot deracemisation of an enol acetate derived from a prochiral cyclohexanone", Tetrahedron Letters, 2001; 42:5959-5962.

Balsara, J. J., et al., "Effect of drugs influencing central serotonergic mechanisms on haloperidol-induced catalepsy", Psychopharmacology, 1979; 62:67-69.

Bastin, R.J., et al., "Salt selection and optimisation procedures for pharmaceutical new chemical entities," Organic Process Research & Development, 2000; 4:427-435.

Birrell, J., et al., "Medial frontal cortex mediates preceptual attentional set shifting in the rat", Journal of Neuroscience, 2000; 20(11):4320-4324.

Bogeso, K.P., et al., "Stereospecific and selective 5-HT2 antagonism is a series of 5-substituted trans-1-piperazino-3-phenylindans," J. Med. Chem., 1993, 36:2761-2770.

Desiraju, G.R., "Cryptic crystallography," Nature Matter, 2002, 1:77-79.

Dinh, P., et al., "Catalytic racemisation of alcohols: applications to enzymatic resolution reactions", Tetrahedron Letters, 1996; 37(42):7623-7626.

Farde, L., et al., "Positron emission tomographic analysis of central D1 and D2 dopamine receptor occupancy in patients treated with classical neuroleptics and clozapine: relation to extrapyramidal side effects", Archives of General Psychiatry, 1992; 49:538-544.

Francotte, E., "Enantioselective chromatography as a powerful alternative for the preparation of drug enantiomers", Journal of Chromatography A, 2001; 906:379-397.

Green, M. F., et al., "The neurocognitive effects of low-dose haloperidol: a two-year comparison with risperidone", Society of Biological Psychiatry, 2002; 51:972-978.

Harvey, P.D., et al., "Studies of cognitive change in patients with schizophrenia following novel antipsychotic treatment", American Journal Psychiatry, 2001; 158:176-184.

(Continued)

*Primary Examiner* — Erich A Leeser
(74) *Attorney, Agent, or Firm* — Mary Catherine Di Nunzio; Margaret M. Buck

(57) ABSTRACT

Crystalline base of compound trans-1-((1R,3S)-6-chloro-3-phenylindan-1-yl)-3,3-dimethylpiperazine, processes for the preparation of purified free base or salts of this compound, pharmaceutical compositions comprising the base and medical use thereof, including for treatment of schizophrenia and other psychotic disorders.

8 Claims, 2 Drawing Sheets

OTHER PUBLICATIONS

Hertel, P., et al., "Repeated administration of the neurotensin analogue NT69L induces tolerance to its suppressant effect on conditioned avoidance behaviour", Eur. J. Pharmacology, 2002; 439:107-111.

Keefe, R. et al., "The brief assessment of cognition in schizophrenia: reliability, sensitivity, and comparison with a standard neurocognitive battery", Schizophrenia Research, 2004; 68:283-297.

Maruzen, "The fourth series of experimental chemistry," The Chemical Society of Japan, 1998; 27:426-439.

Meltzer, H.Y., et al., "The effects of clozapine, risperidone, and olanzapine on cognitive function in schizophrenia", Schizophrenia Bulletin, 1999; 25(2):233-255.

Mitchell, E.S., et al., "5-HT6 receptors: a novel target for cognitive enhancement", Pharmacology & Therapeutics, 2005; 108:320-33.

Price, S. L. "The computational prediction of pharmaceutical crystal structures and polymorphism," Adv. Drug Delivery Rev. 2004; 56:301-19.

Rodefer, J., et al., "PDE10A inhibition reverses subchronic PCP-induced deficits in attentional set-shifting in rats", European J. Neuroscience, 2005; 21:1070-1076.

Chemical Abstract Society No. 94800-10-9, Nov. 16, 1984.

Chemical Abstract Society No. 25086-89-9, Feb. 23, 2011.

Gonzalez-Gomez, J.C. et al. New Arylpiperazine Derivatives with High Affinity for alpha 1A, D2 and 5-HT2A Receptors. Biorg. Med. Chem. Lett. 13:175-178. (2003).

Newman, A. H. Novel pharmacotherapies for cocaine abuse. 1997-2000. Exp. Opin. Ther. Patents. 10 (7):1095-1122 (2000).

Robichaud, A. J. et al. Recent Advances in selective Serotonin Receptor Modulation. Ch. 2. in Ann. Rep. Med. Chem. v. 35:11-20. Raleigh, NC: Academic Press (Elsevier). (2000).

Zhang, A. et al. Recent advances towards the discovery of dopamine receptor ligands. Expert Opin. Ther. Patents. 16(5):587-630. (2006).

Balsara, J. J, et al. Effect of Drugs Influencing Central Serotonergic Mechanisms on Haloperidol-Induced Catalepsy. Psychopharmacol. 1979. 62:67-69.

Bertz, R J. et al. Use of In Vitro and In Vivo Data to Estimate the Likelihood of Metabolic Pharmacokinetic Interactions. Clin. Pharmacokinet. 1997. 32(3):210-258.

Bogeso, K.P. Drug Hunting: The Medicinal Chemistry of 1-Piperazino-3-Phenylindans and Related Compounds. Copenhagen, Denmark: Nørhaven. 1998. (Thesis). ISBN 87-88085-10-4.

Bogeso, K. P. et al. Enhanced D1 Affinity in a Series of Piperazine Ring Substituted 1-Piperazino-3-Arylindans with Potential Atypical Antipsychotic Activity. J. Med. Chem. 1995. 38(22):4380-4392.

Bogeso, K. P. et al. 3-Phenyl-1-indanamines. Potential Antidepressant Activity and Potent Inhibition of Dopamine, Norepinephrine, and Serotonin Uptake. J. Med. Chem. 1985. 28:1817-1828.

Bogeso, K. P. Neuroleptic Activity and Dopamine-Uptake Inhibition in 1-Piperazino-3-phenylindans. J. Med. Chem. 1983. 26(7):935-47.

Carlsson, A. Antipsychotic Drugs, Neurotransmitters, and Schizophrenia. Am. J. Psych. 1978. 135(2):164-173.

Carlsson, L. et al. QTU-Prolongation and Torsades de Pointes Induced by Putative Class III Antiarrhythmic Agents in the Rabbit: Etiology and Interventions. J. Cardiovasc. Pharmacol. 1990. 16:276-285.

Chauret, N. et al. The Use of 3-[2-(N,N-Diethyl-N-Methylammonium)Ethyl]-7-Methoxy-4-Methylcoumarin (AMMC) as a Specific CYP2D6 Probe in Human Liver Microsomes. Drug Metab. Dispos. 2001. 29(9):1196-1200.

Clark, W. M. et al. A Highly Enantioselective Conjugate Reduction of 3-Arylinden-1-ones Using Bakers' Yeast for the Preparation of (S)-3-Arylindan-1-ones. Org. Lett. 1999. 1(11):1839-1842.

Clark, W. M. et al. A Catalytic Enantioselective Synthesis of the Endothelin Receptor Antagonists SB-209670 and SB-217242. A Base-Catalyzed Stereospecific Formal 1,3-Hydrogen Transfer of a Chiral 3-Arylindenol. J. AM. Chem. Soc. 1998. 120:4550-4551.

Cossy, J. et al. Synthesis of Indatraline Using a Suzuki Cross-Coupling Reaction and a Chemoselective Hydrogenation: A Versatile Approach. Synlett. 2003. 10:1515-1517.

Cox, G.B. (ed.) Preparative Enantioselective Chromatography. Oxford, UK: Blackwell Publishing Ltd. 2005.

Darpö, B. Spectrum of Drugs Prolonging QT Interval and the Incidence of Torsades de Pointes. Eur. Heart J. Suppl. 2001. (3 suppl. K):K70-K80.

Davies, H. M. L. et al. Asymmetric Synthesis of (+)-Indatraline Using Rhodium-Catalyzed C-H Activation. Tet. Lett. 2002. 43:4951-4953.

Eder, D. N. CEE-03-310 CeNeS Pharmaceuticals. Curr. Opin. Invest. Drugs. 2002. 3(2): 284-288.

Ereshefsky, L. et al. Serotonin Selective Reuptake Inhibitor Drug Interactions and the Cytochrome P450 System. J. Clin. Psych. 1996. 57(Suppl. 8):17-25.

Froimowits, M. et al. Slow-Onset, Long-Duration 3-(3',4'-Dichlorophenyl)-1-indanamine Monoamine Reuptake Blockers as Potential Medications to Treat Cocaine Abuse, J. Med. Chem. 2000. 43:4981-4992.

Glassman, A. H. et al. Antipsychotic Drugs: Prolonged QTc Interval, Torsade de Pointes, and Sudden Death. Am J Psychiatry. 2001. 158(11):1774-1782.

Gu, X. H. et al. Design, Synthesis, and Monoamine Transporter Binding Site Affinities of Methoxy Derivatives of Indatraline. J. Med. Chem. 2000. 43:4868-4876.

Haleblian, J. et al. Pharmaceutical Applications of Polymorphism. J. Pharmaceut. Sci. 1969. 58(8):911-929.

Hyttel, J. et al. Neurochemical Profile of Lu 19-005, a Potent Inhibitor of Uptake of Dopamine, Noradrenaline, and Serotonin. J. Neurochem. 1985. 44:1615-1622.

Lin, J.H. et al. Role of Pharmacokinetics and Metabolism in Drug Discovery and Development. Pharmacol. Rev. 1997. 49(4):403-449.

Millan, M. J. et al. S18327 (1-(2-[4-(6-Fluoro-1,2-benzisoxazol-3-yl)piperid-1-yl]ethyl)3-phenyl imidazolin-2-one), a Novel, Potential Antipsychotic Displaying Marked Antagonist Properties at α1- and α2-Adrenergic Receptors: I. Receptorial, Neurochemical, and Electrophysiological Profile. J. Pharmacol. Exp. Ther. 2000. 292(1):38-53.

Pedersen, V. et al. Drug Hunting. Ch. 25. In Interviews by D. Healy. The Psychopharmacologists II. London: Arnold. 1999. pp. 561-579.

Raehl, C. L. et al. Drug-Induced Torsade de Pointes. Clin. Pharm. 1985. 4:675-690.

Rendic, S. et al. Human Cytochrome P450 Enzymes: A Status Report Summarizing Their Reactions, Substrates, Inducers, and Inhibitors. Drug Metab. Rev. 1997. 29(1&2):413-580.

Seeman, P. Dopamine Receptors and Psychosis. Sci. Am. 1995. 2:28-37.

Shulman, R. W. et al. Psychotropoic Medications and Cytochrome P450 2D6: Pharmacokinetic Considerations in the Elderly. Can. J. Psychiatry. 1997. 42(suppl. 1):4S-9S.

Sommer, M. B. et al. Application of (2-Cyanoaryl)arylacetonitriles in Cyclization and Annulation Reactions Preparation of 3-Arylindans, 4-Aryl-3,4-dihydronaphthalenes, 4-Arylisoquinolines, 1-Aminonaphthalense, and Heterocyclic Analogues. J. Org. Chem. 1990. 55:4822-4827.

Willner, P. Dopamine and Depression: A Review of Recent Evidence. I. Empirical Studies. Brain Res. Rev. 1983. 6(3):211-224.

Willner, P. Dopamine and Depression: A Review of Recent Evidence. II. Theoretical Approaches. Brain Res. Rev. 1983. 6(3):225-236.

Willner, P. Dopamine and Depression: A Review of Recent Evidence. III. The Effects of Antidepressant Treatments. Brain Res. Rev. 1983. 6(3):237-246.

Woosley, R. L. Cardiac Actions of Antihistamines. Ann. Rev. Pharmacol. Toxicol. 1996. 36:233-252.

Yap, Y. G. et al. The Current Cardiac Safety Situation With Antihistamines. Clin. Exper. Allergy. 1999. 29(suppl. 1):15-24.

Yun, J. et al. Efficient Kinetic Resolution in the Assymetric Hydrosilylation of Imines of 3-Substituted Indanones and 4-Substituted Tetralones. J. Org. Chem 2000. 65:767-774.

International Search Report for International Application No. PCT/DK2006/000088. May 23, 2006.

University of Cambridge "Major advances made in predicting crystal structures", Physics-Condensed Matter. (Nov. 26, 2007); available on line at www.physorg.com/pring1153104.

* cited by examiner

CRYSTALLINE BASE OF TRANS-1-((1R,3S)-6-CHLORO-3-PHENYL-INDAN-1-YL)-3,3-DIMETHYLPIPERAZINE

CROSS-REFERENCE TO RELATED APPLICATION

The present application is a continuation of U.S. Nonprovisional patent application Ser. No. 11/816,394, filed Feb. 12, 2008, which is a national stage application of International Application No. PCT/DK2006/000088 (International Publication No.: WO/2006/086986), filed Feb. 14, 2006, which claims the benefit of Danish Patent Application Serial No. DK PA 2005 00239 and U.S. Provisional Patent Application Ser. No. 60/653,419, both of which were filed Feb. 16, 2005. Each of these applications is herein incorporated by reference in its entirety.

The present invention relates to crystalline base of trans-1-((1R,3S)-6-chloro-3-phenylindan-1-yl)-3,3-dimethylpiperazine, formulations of said base, the use of said base in the preparation of a salt of trans-1-((1R,3S)-6-chloro-3-phenylindan-1-yl)-3,3-dimethylpiperazine, formulations of such salt and the medical use of said base or salt, in particular for treatment of schizophrenia or other diseases involving psychotic symptoms.

BACKGROUND OF THE INVENTION

The compound, which is the subject of the present invention (Compound I, trans-1-((1R,3S)-6-chloro-3-phenylindan-1-yl)-3,3-dimethylpiperazine) has the general formula (I).

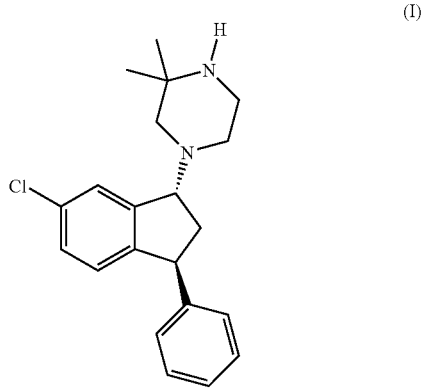

(I)

Compound I and salts thereof, including a fumarate salt and a maleate salt, are described in PCT/DK04/000546 (WO05/016901).

As described in PCT/DK04/000546 the inventors have found that Compound I displays high affinity for dopamine (DA) D1 receptors, DA D2 receptors and for alfa1 adrenoceptors. Furthermore, Compound I was found to be an antagonist at dopamine D1 and D2 receptors, and at serotonin 5-HT2a receptors. As further described in PCT/DK04/000546, Compound I is a relatively weak inhibitor of CYP2D6 (i.e. reduced potential for drug to drug interaction) and has a relatively low effect on the QT interval in a rabbit model (i.e. reduced potential for introducing drug-induced QT interval prolongation and appearance of fatal cardiac arrhythmias, torsade de pointes (TdP), in humans). Additionally, the 5-HT$_2$ antagonistic activity of Compound I suggests that Compound I may have a relatively low risk of extrapyramidal side effects.

The properties outlined above, e.g. binding assays (including alfa1, DA D1 or D2 receptors), efficacy assays (including DA D1 or D2, or serotonin 5-HT$_{2A}$ receptors), CYP2D6 inhibition and QT-interval may be determined as described in PCT/DK04/000546, cf. in particular the "Example" section page 19-24 in the application text as filed for PCT/DK04/000546.

Further, the inventors have found that Compound I did not induce dystonia when tested in pigs sensitized to haloperidol, indicating that Compound I does not possess EPS (extrapyramidal symptoms) response/liability in humans.

PCT/DK04/000546 describes the following medical uses of Compound I: a disease in the central nervous system, including psychosis, in particular schizophrenia (e.g. positive, negative, and/or depressive symptoms) or other diseases involving psychotic symptoms, such as, e.g., Schizophrenia, Schizophreniform Disorder, Schizoaffective Disorder, Delusional Disorder, Brief Psychotic Disorder, Shared Psychotic Disorder as well other psychotic disorders or diseases that present with psychotic symptoms, e.g. mania in bipolar disorder. Also described is the use of Compound I for treatment of anxiety disorders, affective disorders including depression, sleep disturbances, migraine, neuroleptic-induced parkinsonism, or cocaine abuse, nicotine abuse, alcohol abuse and other abuse disorders.

As indicated in PCT/DK04/000546 a group of compounds structurally related to Compound I, i.e. trans isomers of 3-aryl-1-(1-piperazinyl)indanes substituted in the 2- and/or 3-position of the piperazine ring, has been described in EP 638 073; Bøgesø et al. in J. Med. Chem., 1995, 38, 4380-4392 and Klaus P. Bøgesø in "Drug Hunting, the Medicinal Chemistry of 1-piperazino-3-phenylindans and Related Compounds", 1998, *ISBN* 87-88085-10-4I. For example, an enantiomeric pure compound corresponding to formula (I) but differing in that it has an N-methyl group instead of an N-hydrogen on the piperazine has been disclosed in Bøgesø et al. in J. Med. Chem., 1995, 38, 4380-4392, see table 5, compound (−)-38.

None of the above references apart from PCT/DK04/000546 disclose the specific enantiomeric form above (Compound I) or medical use thereof. The trans isomer in the form of the racemate of Compound I is only indirectly disclosed as an intermediate in the synthesis of compound 38 in Bøgesø et al. in J. Med. Chem., 1995, 38, 4380-4392 while medical use of Compound I or its corresponding racemate is not described. Compound I as an intermediate is disclosed in PCT/DK04/000545 (WO05/016900).

Figure 1:
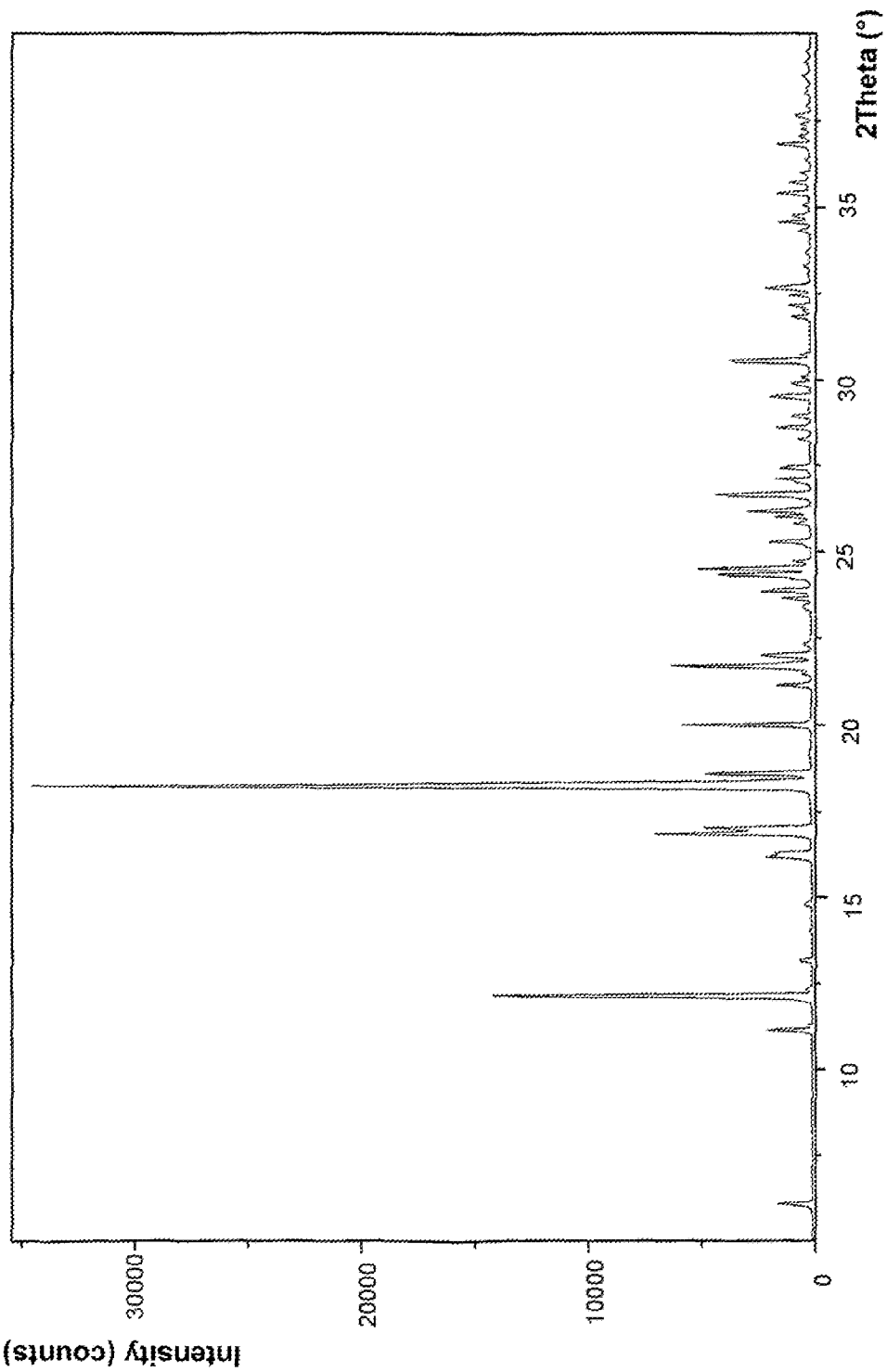
FIG. 1: Shows an X-ray powder diffractogram of a crystalline free base of Compound I (obtained using CuKα$_1$ radiation).

Further details for the figures are revealed in the Examples below.

DETAILED DESCRIPTION OF THE INVENTION

By the methods disclosed in PCT/DK04/000546 Compound I was obtained as an oil. It has now been found that the free base of Compound I can be obtained as a crystalline product which is a favourable solid form of Compound I both for the manufacturing process (e.g. handling and processability properties in general are improved) and for pharmaceutical formulation (e.g. uniform physical and chemical properties of solids are required for formulation purposes).

Furthermore, it has been found that an efficient purification of Compound I may be obtained during the manufacture of Compound I by crystallisation of the base, and thereafter optionally forming a salt of the base. During the synthesis some cis diastereoisomer of Compound I (i.e. 1-((1S,3S)-6-chloro-3-phenylindan-1-yl)-3,3-dimethylpiperazine) may form as an impurity in the final product. The inventors have found that the final content of cis-isomer may be substantially reduced by precipitation of the crystalline base of Compound I. Furthermore, purification as regards other impurities, e.g. detected by HPLC, is significantly enhanced by crystallization of the free base (cf. Example 9 where other impurities than the cis-isomer are reduced from 10% to 1%.)

In contrast to this the inventors have found that it is difficult to obtain solid Compound I in the form of a salt suitable for pharmaceutical formulation, e.g. it has been difficult to prepare a salt of Compound I having a well defined stoichiometric ratio between the acid and Compound I, even upon recrystallisation, and/or which are not having organic solvents or water in the crystal.

Thus, the invention relates to crystalline base of Compound I (formula I below).

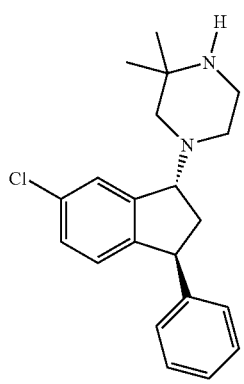

In further embodiments, the crystalline base of Compound I is characterised by one or more of:
(i) an X-Ray powder diffractogram corresponding to that of FIG. 1 as measured using CuK$_{\alpha 1}$ radiation;
(ii) an X-Ray powder diffractogram obtained using CuK$_{\alpha 1}$ radiation ($\lambda$=1.5406 Å) showing peaks at the following 2θ-angles: 6.1, 11.1, 12.1, 16.2, 16.8, 18.3, 18.6, 20.0;
(iii) a DSC thermogram corresponding to that of FIG. 2;
(iv) a DSC trace showing an endotherm with onset about 91-93° C.;
(v) substantially anhydrous and/or solvent free;
(vi) it has a purity of at least 90%, at least 95% or at least 98% as measured by HPLC (area).

Described differently, the invention relates to the free base of the compound of formula (I) [Compound I, trans-1-((1R,3S)-6-chloro-3-phenylindan-1-yl)-3,3-dimethylpiperazine] in a solid form, preferably in a solid form comprising crystalline free base of Compound I, e.g. in a solid form that is at least 80% crystalline, at least 90% crystalline, at least 95% crystalline or at least 98% crystalline. The following embodiments described below for "the crystalline base of Compound I", i.e. method of manufacturing, pharmaceutical compositions, medical uses, such as use of the free base of the invention in medicine, and methods of treatments is meant also to apply to the solid free base of the invention as further embodiments of the invention.

As used herein, the term "solid form" in connection with Compound I refers to any solid form of Compound I exemplified by crystalline form and amorphous solid form as well as mixtures thereof, in contrast, e.g., to Compound I in the form of an oil.

As used herein expressions like "characterized by the X-Ray powder diffractogram shown in FIG. 1) as measured using CuK$_{\alpha 1}$" mean the crystalline form of Compound I having an X-ray powder diffractogram substantially similar to FIG. 1, i.e. exhibiting an X-ray powder diffraction pattern as exemplified in that Figure and measured under comparable conditions as described herein or by any comparable method using CuK$_{\alpha 1}$ radiation, such that margins of analytical variations are taken into consideration.

That the crystalline base is substantially anhydrous and solvent free may e.g. be judged from TGA analysis, e.g. as described in the Examples herein.

In one embodiment, the crystalline base of the invention is not a solvate, i.e. the crystalline base of the invention does not contain crystal bound solvent molecules.

The compound of formula (I) in racemic form may, e.g., be prepared analogously to the methods outlined in EP 638 073, and in Bøgesø et al. J. Med. Chem., 1995, 38, page 4380-4392 followed by optical resolution of the racemic compound by crystallisation of diastereomeric salts thereby obtaining the enantiomer of formula (I), i.e. Compound I. Alternatively, Compound I may be obtained by a method as described in the international patent application PCT/DK04/000546, i.e. from enantiomeric pure V, i.e. compound Va ((1S,3S)-6-chloro-3-phenylindan-1-ol, see below). Compound V has the following formula (V) with cis configuration:

Compound Va has the following formula (Va), i.e. also with cis configuration:

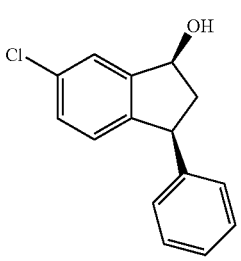

As indicated above during the synthesis some cis diastereoisomer of Compound I is formed as an impurity. The cis form of Compound I may alternatively or additionally, e.g., be removed by precipitation of a suitable salt of the compound of formula Compound I, e.g. HCl or a salt of an organic acid, such as an organic diacid, e.g. a fumarate salt or a maleate salt of the compound of formula (I), optionally followed by one or more re-crystallisations.

Broadly speaking, the crystalline base of Compound I may be prepared by crystallising the base of Compound I from a solvent, i.e. a suitable single solvent or a suitable mixture of solvents. Accordingly, the term "a solvent" as used herein include both a single solvent or a mixture of different solvents. It is understood that the solvent may comprise water as the case may be, e.g. about 0-10% water. Compound I may be prepared using methods known in the art, such as those described herein.

By way of general guidance, Compound I may be mixed with a suitable solvent which may be heated to facilitate the dissolution of Compound I. Preferred temperatures in this regard may range from about 30° C. to the boiling point (i.e., the reflux temperature) of the solvent or solvent mixtures. More preferred temperatures may range from about 60° C. to the boiling point of the solvent. The resulting mixture of solvent and Compound I may be cooled to initiate and/or continue crystallisation. The mixture is preferably cooled (i.e. including natural cooling to ambient temperature) to a temperature, which ranges from, e.g., about minus 20° C. to about 20° C., e.g. to ambient temperature. The precipitated solids may be isolated from the cooled mixture by for example filtration or centrifugation, and if necessary washed with a suitable solvent such as, but not limited to, the solvent employed for the crystallisation, and dried at ambient pressure or "in vacuo" at ambient or slightly elevated temperature, e.g. under a nitrogen purge. Seed crystals may be added to any crystallisation mixture to promote crystallisation.

Accordingly, the invention in a further aspect relates to a method for preparing crystalline base of Compound I in which method the crystalline base of Compound I is formed in a solvent, e.g. of ethyl acetate or heptane or a mixture hereof. In one embodiment, the crystalline base of Compound is prepared by crystallisation of the base of Compound I from a solvent, e.g. ethyl acetate or heptane or a mixture of these, and separating the solvent form the obtained crystalline base of Compound I.

The invention also relates to a method for the manufacturing of Compound I, characterised in that the base of Compound I is set free and precipitated to obtain the free base of Compound I in crystalline form, optionally re-crystallised one or more times, and then transferred into a salt of Compound I. In one embodiment, the base of Compound I is set free from a crude salt or crude mixture of Compound I. The term crude mixture in this context means that the mixture comprises impurities, e.g. the diastereomer of Compound I and Compound V(a) and unreacted reactants, which it is desired to remove. The crude mixture may be separated directly from the reaction mixture, or the crude reaction mixture may have been subjected to some initial purification. Accordingly, the invention also relates to salts of Compound I obtained by a process comprising the steps of: (i) crystallising the base of Compound I, and (ii) forming a salt from the base, which salt is also termed "a salt of the invention".

The invention also relates to a method for the manufacturing of the following compound of formula II [trans-4-((1R, 3S)-6-chloro-3-phenylindan-1-yl)-1,2,2-trimethylpiperazine; Compound II], or a salt thereof,

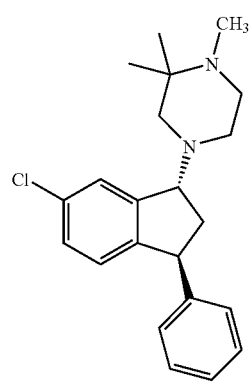

(II)

comprising the step of methylation at the secondary amine of Compound I to obtain the free base of Compound II, and alternatively precipitating said compound as a salt, wherein Compound I is produced according to a method of the invention as described herein, i.e. in particular comprising a step in which Compound I is converted to a crystalline free base of Compound I. The synthesis of Compound II from Compound I is described in WO05/016900. The salt of Compound II may, e.g., be a succinate or a malonate salt, e.g. a hydrogen succinate salt or a hydrogen malonate salt as described in WO05/016900. In further embodiments, Compound II or a salt thereof may subsequently by formulated into a pharmaceutical composition.

Thus, in further aspects the invention provides the following embodiments: crystalline base of Compound I obtainable, in particular obtained, by a method as described herein; a salt of Compound I obtainable, in particular obtained, by a method as described herein, e.g. a fumarate or a maleate or a hydrochloric salt of Compound I; a pharmaceutical composition comprising such base of Compound I or a salt of Compound I obtainable or obtained by a method of the invention; and the medical uses as described herein for these Compound I products.

The properties of Compound I indicate that it will be useful as a pharmaceutical. Accordingly, the present invention further relates to a pharmaceutical composition of the crystalline base of Compound I or a salt of the invention, together with, e.g., at least one pharmaceutically acceptable carrier, filler or diluent.

The invention also relates to the medical use of such crystalline base or salt of the invention and compositions, e.g. for the treatment of a disease in the central nervous system, including psychosis, in particular schizophrenia or other diseases involving psychotic symptoms, such as, e.g., Schizophrenia, Schizophreniform Disorder, Schizoaffective Disorder, Delusional Disorder, Brief Psychotic Disorder, Shared Psychotic Disorder as well other psychotic disorders or diseases that present with psychotic symptoms, e.g. mania in bipolar disorder.

The present invention also relates to use of the crystalline base of Compound I or a salt of the invention, for treatment of a disease selected from the group consisting of anxiety disorders, affective disorders including depression, sleep disturbances, migraine, neuroleptic-induced parkinsonism, cocaine abuse, nicotine abuse, alcohol abuse and other abuse disorders.

In a preferred embodiment, the present invention relates to a method of treating Schizophreniform Disorder, Schizoaffective Disorder, Delusional Disorder, Brief Psychotic Disorder, Shared Psychotic Disorder or mania in bipolar disorder, comprising administering a therapeutically effective amount of the crystalline base of Compound I or a salt of the invention.

A further embodiment of the invention relates to a method of treating positive symptoms of schizophrenia comprising administering a therapeutically effective amount of the crystalline base of Compound I or a salt of the invention. Another embodiment of the invention relates to a method of treating negative symptoms of schizophrenia comprising administering a therapeutically effective amount of the crystalline base of Compound I or a salt of the invention. A further embodiment of the invention relates to a method of treating depressive symptoms of schizophrenia comprising administering a therapeutically effective amount of the crystalline base of Compound I or a salt of the invention. A further aspect of the invention relates to a method of treating mania and/or maintenance of bipolar disorder comprising administering a therapeutically effective amount of the crystalline base of Compound I or a salt of the invention.

In the present context, in particular for the pharmaceutical uses, it is understood that when specifying the enantiomer form as done in formula (I) for Compound I, then the compound is relatively stereochemically pure, preferably the enantiomeric excess is of at least 60%, at least 70%, and more preferably at least 80% (80% enantiomeric excess means that the ratio of I to its enantiomer is 90:10 in the mixture in question) at least 90%, at least 96%, or preferably at least 98%.

In a preferred embodiment, the diastereomeric excess of Compound I is at least 90% (90% diastereomeric excess means the ratio of Compound I to cis-1-((1S,3S)-6-chloro-3-phenylindan-1-yl)-3,3-dimethylpiperazine is 95:5), at least 95%, at least 97%, or at least 98%.

A further aspect of the invention relates to a method of treatment as described herein, wherein the patient treated with the crystalline base of Compound I or a salt of the invention is also treated with at least one other medicament. A particular relevant embodiment in this connection, is treatment with other medicaments being metabolised by CYP2D6 or at least having such potential. In a suitable embodiment, the other medicament is an antipsychotic. Accordingly, one embodiment relates to the use of the crystalline base or a salt of the invention or pharmaceutical composition of the invention for treating a patient suffering from schizophrenia or other psychoses who is also treated with other medicament(s), e.g. where this other medicament is an antipsychotic.

In another embodiment, the invention relates to the use of the crystalline base of Compound I, a salt of the invention, or pharmaceutical composition of the invention for treating a patient suffering from schizophrenia or other psychoses who is a substance abuser, e.g. of alcohol or narcotics.

The crystalline base of the invention, or the salt of the invention, or pharmaceutical composition of the invention may be administered in any suitable way e.g. orally, buccal, sublingual or parenterally, and the compound or may be presented in any suitable form for such administration, e.g. orally in the form of tablets, capsules, powders, syrups, solutions or dispensions, or parenterally in the form of dispersions or solutions for injection. In one embodiment, the crystalline base of the invention is administered in the form of a solid pharmaceutical entity, suitably as a tablet or a capsule.

Methods for the preparation of solid pharmaceutical preparations are well known in the art. Tablets may thus be prepared by mixing the active ingredient with ordinary adjuvants, fillers and diluents and subsequently compressing the mixture in a convenient tabletting machine. Examples of adjuvants, fillers and diluents comprise microcrystalline cellulose, corn starch, potato starch, lactose, mannitol, sorbitol talcum, magnesium stearate, gelatine, lactose, gums, and the like. Any other adjuvant or additive such as colourings, aroma, preservatives, etc. may also be used provided that they are compatible with the active ingredients.

In particular, the tablet formulations according to the invention may be prepared by direct compression of Compound I in admixture with conventional adjuvants or diluents. Alternatively, a wet granulate or a melt granulate of Compound I, optionally in admixture with conventional adjuvants or diluents may be used for compression of tablets.

Solutions for injections may be prepared by solving the active ingredient and possible additives in a part of the solvent for injection, preferably sterile water, adjusting the solution to the desired volume, sterilisation of the solution and filling in suitable ampoules or vials. Any suitable additive conventionally used in the art may be added, such as tonicity agents, preservatives, antioxidants, solubilising agents, etc. Alternatively the crystalline free base may be dissolved in a digestible or non-digestible oil, mixtures hereof or similar, to prepare a intramuscular depot formulation capable of releasing the active ingredient over a prolong period of time.

The daily dose of the compound of formula (I) above, calculated as the free base, is suitably between 1.0 and 160 mg/day, more suitable between 1 and 100 mg, e.g. preferably between 2 and 55 mg.

As indicated above the invention in particular relates to:
crystalline base of Compound I
a salt of the invention, i.e. a salt of compound I prepared from the crystalline base of Compound I;
a pharmaceutical compositions as described herein comprising the crystalline base Compound I or a salt of the invention;
a medical use as described herein for Compound I;
wherein Compound I is having an enantiomeric excess of at least 60% (60% enantiomeric excess means that the ratio of Compound I to its enantiomer is 80:20 in the mixture in question), at least 70%, at least 80%, at least 85%, at least 90%, at least 96%, preferably at least 98%.

One embodiment relates to crystalline base of Compound I, or a salt of the invention or pharmaceutical composition of the invention and the uses as described herein, wherein Compound I is having a diastereomeric excess of at least 10% (10% diastereomeric excess means that the ratio of Compound I to the cis-(1S,3S) diastereoisomer is 55:45 in the mixture in question), at least 25%, at least 50%, at least 70%, at least 80%, at least 90%, at least 95%, at least 97%, preferably at least 98%.

The term "treatment" in connection with a disease as used herein also includes prevention as the case may be. The term "disease" as used herein also includes a disorder as the case may be.

The invention will be illustrated in the following non-limiting examples.

EXAMPLES

Analytical Methods

The enantiomeric excess of Compound (Va) in Example 1 is determined by chiral HPLC using a CHIRALCEL® OD column, 0.46 cm ID×25 cm L, 10 µm at 40° C. n-Hexan/ethanol 95:5 (vol/vol) is used as mobile phase at a flow rate of 1.0 ml/min, detection is performed using a UV detector at 220 nm.

The enantiomeric excess of Compound (I) may be determined by fused silica capillary electrophoresis (CE) using the following conditions: Capillar: 50 µm ID×48.5 cm L, run buffer: 1.25 mM β cyclo dextrin in 25 mM sodium dihydrogen phosphate, pH 1.5, voltage: 16 kV, temperature: 22° C., injection: 40 mbar for 4 seconds, detection: column diode array detection 195 nm, sample concentration: 500 µg/ml. In this system, Compound I has a retention time of approximately 10 min, and the other enantiomer has a retention time of approximately 11 min.

$^1$H NMR spectra is recorded at 500.13 MHz on a Broker Avance DRX500 instrument or at 250.13 MHz on a Bruker AC 250 instrument. Chloroform (99.8% D) or dimethyl sulfoxide (99.8% D) is used as solvents, and tetramethylsilane (TMS) is used as internal reference standard.

The purity of Compound I is determined by HPLC (e.g. also the cis/trans ratio) using a Luna C18(2) 150*4.6 mm (3 µm) column at 40° C. The mobile phase is phosphate buffer pH7.4/acetonitril 40/60, run time 60 min, and after 32 min a gradient of acetonitril/water 90/10 is applied. Detection is performed using a UV detector at 220 nm.

The cis/trans ratio of Compound I and key intermediates may also be determined using $^1$H NMR as described in, e.g., Bøgesø et al., *J. Med. Chem.* 1995, 38, 4380-4392 (page 4388, right column). Generally, a content of approximately 1% of the undesired isomer can be detected by NMR. The Melting points are measured using Differential Scanning Calorimetry (DSC). The equipment is a TA-Instruments DSC-Q1000 calibrated at 5°/min to give the melting point as onset value. About 2 mg of sample is heated 5°/min in a loosely closed pan under nitrogen flow.

Thermo gravimetric analysis (TGA) used for estimation of solvent/water content of dried material is performed using a TA-instruments TGA-Q500. 1-10 mg sample is heated 10°/min in an open pan under nitrogen flow.

X-Ray powder diffractograms were measured on a PANalytical X'Pert PRO X-Ray Diffractometer using CuK$_{\alpha 1}$ radiation. The samples were measured in reflection mode in the 2θ-range 5-40° using an X'celerator detector.

Optical rotation is measured on a polarimeter, Perkin Elmer model 241.

Synthesis

Example 1

Synthesis of (1S,3S)-6-chloro-3-phenylindan-1-ol (Va) by Use of Chiral Chromatography Racemic cis-6-chloro-3-phenylindan-1-ol (V) (prepared as described in PCT/DK04/000546, i.e. adapting the method described in Bøgesø et al. *J. Med. Chem.* 1995, 38, 4380-4392 using ethanol as solvent, and performing the reaction at approximately 0° C.) (492 grams) is resolved by preparative chromatography, using a CHIRALPAK® AD column, 10 cm ID×50 cm L, 10 µm at 40° C. Methanol is used as mobile phase at a flow rate of 190 ml/min, detection is performed using a UV detector at 287 nm. The racemic alcohol (V) is injected as a 50,000 ppm solution in methanol; 90 ml is injected with intervals of 28 min. All the fractions, which contain the title compound with more than 98% enantiomeric excess, are combined and evaporated to dryness using a rotary evaporator, followed by drying in vacuo at 40° C. Yield 220 grams as a solid. Elemental analysis and NMR conform to the structure, the enantiomeric excess is higher than 98% according to chiral HPLC, $[\alpha]_D^{20}$ +44.5° (c=1.0, methanol).

Example 2

Synthesis of (1S,3S)-3,5-dichloro-1-phenylindan

Cis-(1S,3S)-6-chloro-3-phenylindan-1-ol (Va) (204 grams) obtained as described in Example 1 is dissolved in THF (1500 ml) and cooled to −5° C. Thionyl chloride (119 grams) is added dropwise as a solution in THF (500 ml) over a period of 1 h. The mixture is stirred at room temperature over night. Ice (100 g) is added to the reaction mixture. When the ice has melted the water phase (A) and the organic phase (B) are separated, and the organic phase B is washed twice with aqueous saturated sodium bicarbonate (200 ml). The aqueous sodium bicarbonate phases are combined with water phase A, adjusted to pH 9 with sodium hydroxide (28%), and used to wash the organic phase B once again. The resulting aqueous phase (C) and the organic phase B are separated, and the aqueous phase Cis extracted with ethyl acetate. The ethyl acetate phase is combined with the organic phase B, dried with magnesium sulphate, and evaporated to dryness using a rotary evaporator, giving the title compound as an oil. Yield 240 grams, which is used directly in the example 5a. Cis/trans ratio 77:23 according to NMR.

Example 3

Synthesis of 3,3-dimethylpiperazin-2-one

Potassium carbonate (390 grams) and ethylene diamine (1001 grams) are stirred with toluene (1.50 l). A solution of ethyl 2-bromoisobutyrate (500 grams) in toluene (750 ml) is added. The suspension is heated to reflux over night, and filtered. The filter cake is washed with toluene (500 ml). The combined filtrates (volume 4.0 l) are heated on a water bath and distilled at 0.3 atm. using a Claisen apparatus; first 1200 ml distillate is collected at 35° C. (the temperature in the mixture is 75° C.). More toluene is added (600 ml), and another 1200 ml distillate is collected at 76° C. (the temperature in the mixture is 80° C.). Toluene (750 ml) is added again, and 1100 ml of distillate is collected at 66° C. (temperature in the mixture 71° C.). The mixture is stirred on an ice bath and inoculated, whereby the product precipitates. The product is isolated by filtration, washed with toluene, and dried over night in a vacuum oven at 50° C. Yield 171 g (52%) of 3,3-dimethylpiperazin-2-one. NMR consistent with structure.

Example 4

Synthesis of 2,2-dimethylpiperazine

A mixture of 3,3-dimethylpiperazin-2-one (8.28 kg, 64.6 mol, large scale preparation analogous to the preparation described in to Example 3) and tetrahydrofuran (THF) (60 kg) is heated to 50-60° C. giving a slightly unclear solution. THF (50 kg) is stirred under nitrogen, and LiAlH$_4$ (250 g, in a soluble plastic bag) is added, which gives a slow evolution of gas. After gas evolution has ceased, more LiAlH$_4$ is added (a total of 3.0 kg, 79.1 mol, is used), and the temperature rises from 22° C. to 50° C. because of an exoterm. The solution of 3,3-dimethylpiperazin-2-one is added slowly over 2 hours at 41-59° C. The suspension is stirred for another hour at 59° C. (jacket temperature 60° C.). The mixture is cooled, and water (3 l) is added over two hours, keeping the temperature below 25° C. (it is necessary to cool with a jacket temperature of 0° C.). Then aqueous sodium hydroxide (15%, 3.50 kg) is added over 20 minutes at 23° C., cooling necessary. More water (9 l) is added over half an hour (cooling necessary), and the mixture is stirred over night under nitrogen. Filter agent Celite (4 kg) is added, and the mixture is filtered. The filter cake is washed with THF (40 kg). The combined filtrates are concentrated in the reactor until the temperature in the reactor is 70° C. (distillation temperature 66° C.) at 800 mbar. The remanence (12.8 kg) is further concentrated on a rotary evaporator to approximately 10 l. Finally, the mixture is fractionally distilled at atmospheric pressure, and the product is collected at 163-4° C. Yield 5.3 kg (72%). NMR complies with the structure.

Example 5a

Synthesis of trans-1-((1R,3S)-6-chloro-3-phenylindan-1-yl)-3,3-dimethylpiperazinium (Compound I) hydrogen maleate salt Cis-(1S,3S)-3,5-dichloro-1-phenylindan (240 g) is dissolved in butan-2-one (1800 ml). Potassium carbonate (272 g) and 2,2-dimethyl piperazine (prepared as described in Example 4) (113 g) are added and the mixture is heated at reflux temperature for 40 h. To the reaction mixture is added diethyl ether (2 l) and hydrochloric acid (1M, 6 l). The phases are separated, and pH in the water phase is lowered from 8 to 1 with concentrated hydrochloric acid. The water phase is used to wash the organic phase once again in order to ensure, that all product is in the water phase. Sodium hydroxide (28%) is added to the water phase until pH is 10, and the water phase is extracted twice with diethyl ether (2 l). The diethyl ether extracts are combined, dried with sodium sulphate, and evaporated to dryness using a rotary evaporator. Yield 251 grams of free base of Compound I as an oil. Cis/trans ratio, 18:82 according to NMR. The crude oil (ca. 20 grams) was further purified by flash chromatography on silicagel (eluent: ethyl acetate/ethanol/triethylamine 90:5:5) followed by evaporation to dryness on a rotary evaporator. Yield 12 grams of free base of Compound I as an oil (cis/trans ratio, 10:90 according to NMR).

The oil is dissolved in ethanol (100 ml), and to this solution is added a solution of maleic acid in ethanol to pH 3. The resulting mixture is stirred at room temperature for 16 hours, and the formed precipitate is collected by filtration. The volume of ethanol is reduced and another batch of precipitate is collected. Yield 3.5 gram solid, i.e. Compound I hydrogen maleate salt (no cis isomer is detected according to NMR) of the title compound. Enantiomeric excess according to CE is >99%. Melting point 175-178° C. NMR complies with the structure.

Example 5b

Synthesis of trans-1-((1R,3S)-6-chloro-3-phenylindan-1-yl)-3,3-dimethylpiperazinium (Compound I) hydrogen chloride salt Cis-(1S,3S)-3,5-dichloro-1-phenylindan (large scale preparation analogous to the preparation described in example 2) (50.9 kg) is dissolved in MIBK (248 kg). Potassium carbonate (56.8 kg) and 2,2-dimethyl piperazine (29.6 kg) are added and the mixture is heated to 100° C. temperature for 8 hour. The reaction mixture is cooled to room temperature before insoluble inorganic material is removed by filtration. The filtrate is subsequent washed with water (520 l), the phases are separated and pH of the organic phase is adjusted to a value between 3-6 by slow addition of hydrogen chloride (15.4 kg 37% aqueous solution), during the addition the product separates. The product is filtered on a nutsche, and the filter cake is washed by MIBK (100 kg) and cyclohexane (80 kg). The product is dried at 50° C. and 0.05 bar for 12 hours.

Yield: 40 kg. Compound I (no cis-isomer is detected according to NMR-analysis). Enantiomeric excess according to CE is >99%. NMR spectrum complies with the structure.

Example 6a

Synthesis of the Free Base of Compound I from a Hydrogen Maleate Salt

A mixture of trans-1-((1R,3S)-6-chloro-3-phenylindan-1-yl)-3,3-dimethylpiperazinium hydrogen maleate (9.9 grams), concentrated aqueous ammonia (100 ml), brine (150 ml) and ethyl acetate (250 ml) is stirred at room temperature for 30 min. The phases are separated, and the aqueous phase is extracted with ethyl acetate once more. The combined organic phases are washed with brine, dried over magnesium sulphate, filtered and evaporated to dryness in vacuo. Yield 7.5 grams of Compound I as an oil, which may solidify on standing. NMR complies with the structure.

Example 6b

Synthesis of the Free Base of Compound I from a Hydrogen Chloride Salt

The free base of Compound I was prepared as described in example 6a by the use of trans-1-((1R,3S)-6-chloro-3-phenylindan-1-yl)-3,3-dimethylpiperazinium hydrogen chloride as substitute for trans-1-((1R,3S)-6-chloro-3-phenylindan-1-yl)-3,3-dimethylpiperazinium hydrogen maleate.

Yield of Compound I was 9.0 grams starting from 10.2 grams of trans-1-((1R,3S)-6-chloro-3-phenylindan-1-yl)-3,3-dimethylpiperazinium hydrochloride.

Example 7a

Preparation of Crystalline Base of Compound I from 6a

Compound I (9.0 grams obtained as described in Example 6a) was dissolved in ethyl acetate (30 ml), and heptane (75 ml) was subsequently added to the solution. The solution was left with stirring for 4-16 hours. In some cases crystallisation was observed, and the crystalline material was collected by filtration. In other cases, crystallisation was not observed, and a part of the solvent was removed by distillation. The distillation was stopped when distillation temperature changed from the boiling point of ethyl acetate to the boiling point of heptane. The remaining solution was left to cool to room temperature at ambient temperature and prior to filtration on a water/ice bath. The crystallisation could be initiated by scratching with a glass spatula or by seeding. The crystalline Compound I was isolated by filtration. Yield 6.8 grams (74%). NMR complies with the structure. Melting point: 92.4° C. (DSC onset temperature), enantiomeric excess according to CE is >99%.

Example 7b

Preparation of Crystalline Base of Compound I from 6b

Prepared as described in example 7a starting with 9.0 grams of crude base. Yield 6.8 grams. Melting point 92.3° C. (DSC onset temperature) and enantiomeric excess determined by CE is >99%.

Example 8

Characterisation of the Crystalline Base of Compound I

The crystalline base of Compound I obtained by a method as described in Example 7a and 7b had the X-ray powder diffractogram (XRPD) shown in FIG. 1 and was characterized by to the following reflections (peaks) in the X-Ray powder diffractogram as measured using CuK$\alpha_1$ radiation at 2-theta angles: 6.1, 11.1, 12.1, 16.2, 16.8, 18.3, 18.6, 20.0.

Figure 2:
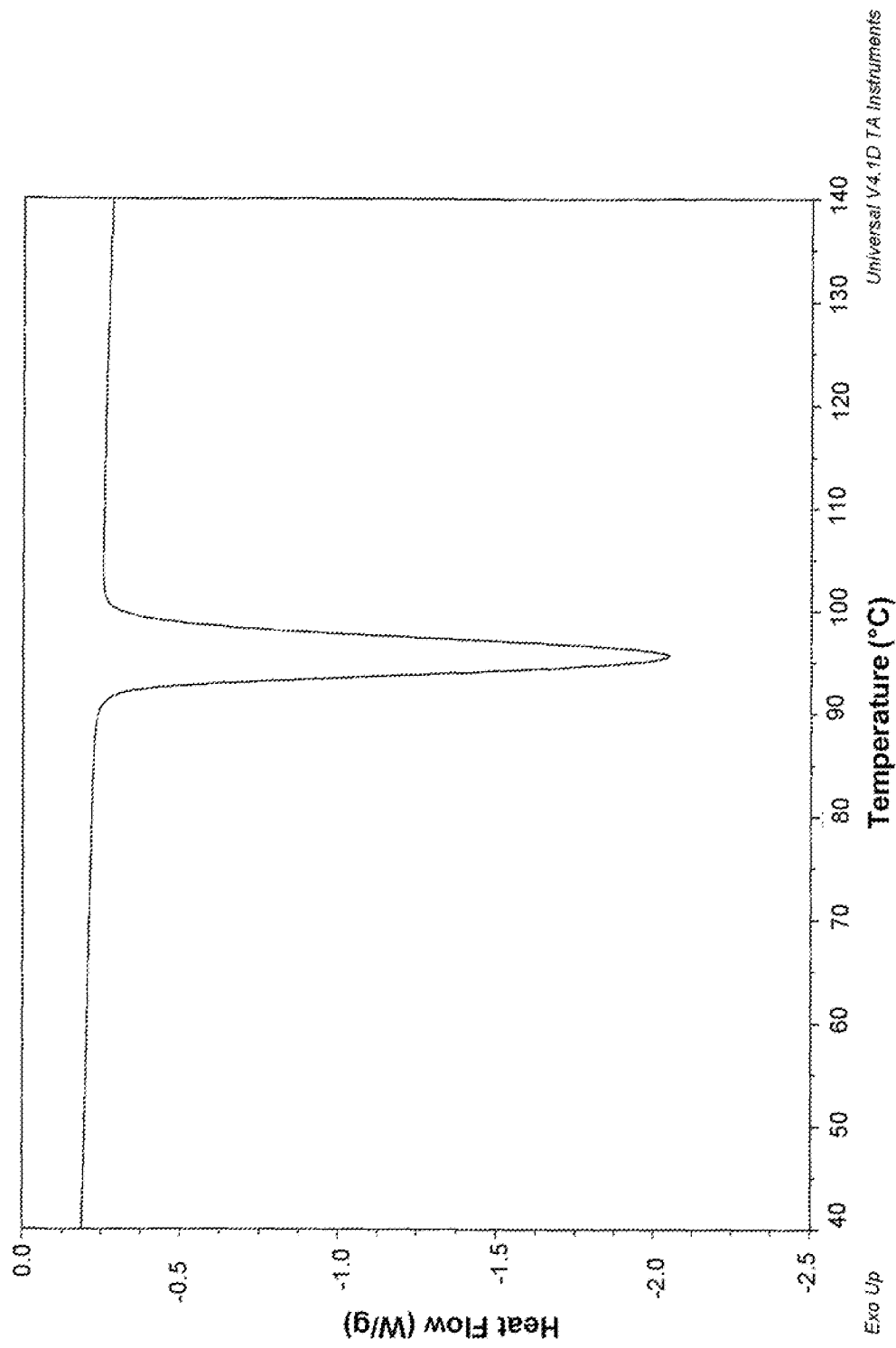
FIG. 2: Shows a DSC thermogram of a crystalline free base of Compound

The crystalline base further had a DSC thermogram corresponding to that of FIG. 2 and a DSC trace showing an endotherm with onset about 91-93° C.

The crystalline based obtained was anhydrous and solvent free as judged from TGA analysis.

Example 9

Preparation of Crystalline Base of Compound I from Crude Compound I from Example 5a Compound I (2.0 grams of crude oil obtained as described in Example 5a, purity as determined by HPLC: 73% area, cis/trans ratio of 17/73) was dissolved in ethyl acetate (5 ml), and heptane (10 ml) was subsequently added to the solution. A part of the solvent was removed by distillation, and the remaining solution was added a spatula of crystalline Compound I (obtained from 7a or 7b). The resulting mixture was left at ambient temperature for 16 hours. The crystalline Compound I was isolated by filtration.

NMR complies with the structure. HPLC Purity (area %): 98%, Content of the cis-isomer: 1%. Enantiomeric excess according to CE is >99%.

The invention claimed is:

1. A method for the treatment of a disease, comprising administering a therapeutically effective amount of the crystalline base of Compound I having formula (I):

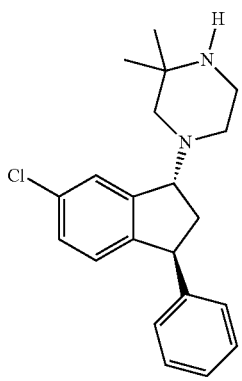

(I)

wherein the disease is selected from the group consisting of a disease involving a psychotic symptom, schizophrenia, an anxiety disorder, an affective disorder and an abuse disorder.

2. The method of claim 1, wherein the disease is schizophrenia or a disease involving a psychotic symptom.

3. The method of claim 2, wherein the schizophrenia comprises one or more positive symptoms, negative symptoms, depressive symptoms, or a combination thereof.

4. A method for treatment of a disease comprising administering a therapeutically effective amount of the crystalline base of Compound I having formula (I):

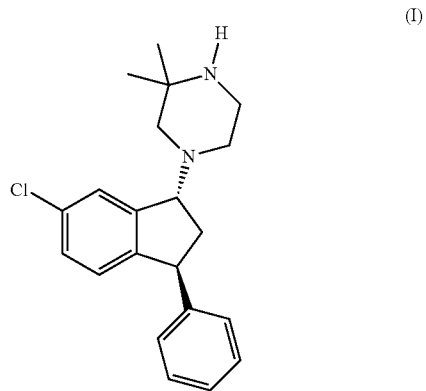 [SMILES: CC1(C)CN([C@@H]2C[C@@H](c3ccccc3)c3ccc(Cl)cc32)CCN1]

(I)

wherein the disease is selected from the group consisting of schizophrenia, schizophreniform disorder, schizoaffective disorder, delusional disorder, brief psychotic disorder, shared psychotic disorder, and mania in bipolar disorder.

5. The method of claim 1, wherein the affective disorder is depression.

6. The method of claim 1, wherein the abuse disorder is cocaine abuse, nicotine abuse, or alcohol abuse.

7. The method of claim 1, wherein a patient treated with the crystalline base of Compound I is also under treatment with at least one other medicament.

8. The method of claim 4, wherein a patient treated with the crystalline base of Compound I is also under treatment with at least one other medicament.

* * * * *